United States Patent [19]

Vesely

[11] Patent Number: 5,691,310
[45] Date of Patent: Nov. 25, 1997

[54] METHODS OF TREATMENT USING PROANF PEPTIDES

[76] Inventor: David L. Vesely, 5020 Londonderry Dr., Tampa, Fla. 33647

[21] Appl. No.: 401,246

[22] Filed: Mar. 9, 1995

Related U.S. Application Data

[63] Continuation-in-part of Ser. No. 799,211, Nov. 14, 1991, abandoned, which is a continuation-in-part of Ser. No. 517,252, May 1, 1990, abandoned, which is a continuation of Ser. No. 102,477, Sep. 29, 1987, abandoned.

[51] Int. Cl.$^6$ ............................ A61K 38/00; C07K 5/00; C07K 7/00
[52] U.S. Cl. ............................ 514/12; 514/13; 530/324; 530/326
[58] Field of Search ............................ 514/12, 13; 530/324, 530/326

*Primary Examiner*—Avis M. Davenport

[57] ABSTRACT

A method of treatment of hypertension, congestive heart failure, pulmonary edema, nephrotic syndrome, acute and chronic renal failure, toxemia of pregnancy, hepatic cirrhosis, and/or hyperkalemia. Humans or other mammals are administered an effective amount of peptide(s) consisting of amino acids 1–30 (proANF 1–30), amino acids 31–67 (proANF 31–67) and amino acids 79–98 (i.e., proANF 79–98) of the human sequence of the atrial natriuretic factor (ANF) prohormone. Pharmaceutical compositions include such peptides in an effective concentration within a pharmaceutically acceptable liquid or solid carrier.

25 Claims, 8 Drawing Sheets

METHODS OF TREATMENT USING PROANF PEPTIDES

This application is a continuation-in-part of U.S. Ser. No. 07/799,211 filed Nov. 14, 1991, now abandoned, which is a continuation-in-part of U.S. Ser. No. 07/517,252 filed May 1, 1990, now abandoned, which is a continuation of U.S. Ser. No. 07/102,477, filed Sep. 29, 1987, now abandoned.

The present invention is directed to methods for pharmaceutical treatment of 1) congestive heart failure, including a severe form called pulmonary edema, nephrotic syndrome, renal failure, hepatic cirrhosis and toxemia of pregnancy each of which are characterized by retention of sodium and water and 2) treatment of high blood pressure and myocardial ischemia of mammals including humans with new peptides that increase sodium and water excretion and also lower blood pressure. One of these new peptides, i.e., proANF 79–98 has strong potassium excreting properties which direct it to the treatment of hyperkalemia (i.e., high blood potassium) associated with acidosis, digitalis overdose, succinylcholine, insulin deficiency, acute and chronic renal failure, Addison's disease (i.e., adrenal insufficency) and the syndromes of hyperkalemic periodic paralysis, and hyporeninemic hypoaldosteronism. Specifically, the invention is directed to methods of treatment of mammals (especially humans) by administration of pharmaceutical compositions containing one or more of three peptide hormones derived from the 98 amino acid amino terminal polypeptide of the human sequence of 126 amino acid atrial natriuretic peptide prohormone (hereafter referred to as proANF).

BACKGROUND OF THE INVENTION

DeBold et al. in Life Sci. 28, 89–94, (1981) demonstrated that crude rat heart atrium extracts increased natriuresis and lowered blood pressure when intravenously injected into other rats which suggested that the heart made one or more blood pressure and/or sodium excreting hormones. This substance(s) was called atrial natriuretic factor (ANF) since 1) the substance was obtained from the atrium of the heart and had more biological activity than extracts of the ventricle of the heart, 2) it caused a natriuresis (i.e., enhanced sodium excretion) and 3) it was unknown at that time that the factor was a peptide (s) (DeBold et al., ibid).

The amino acid sequence of the polypeptide prohormone containing the biologically active hormones was then determined for rat (Yamanaka et al., Nature 309:719–722, 1984; Maki et al., Nature 309:722–724, 1984; Zivin et al., Proc. Natl. Acad. Sci. 81:6325–6329, 1984; Seidman et al., Science 225:324–326) and humans (Oikawa et al., Nature 309:724–726, 1984; Zivin et al., ibid). It was found that the amino acids (a.a.) making up the peptides derived from the rat and human atrial natriuretic factor prohormones were different. Further investigation revealed that the ANF prohormone is synthesized within the atrial myocyte as a 151 amino acid (a.a.) preprohormone. This preprohormone is processed within the endoplasmic reticulum of humans to form a prohormone consisting of 126 a.a. after removal of the 25 a.a. signal peptide from its N-terminal end. This 126 a.a. ANF prohormone is the main storage form of atrial natriuretic peptides within the heart (and within other tissues).

At first it was thought that only the C-terminus (i.e., ANF) of ANF prohormone circulated. Before any portion of the rest of the prohormone was known to circulate Dr. Frossman patented the whole rat prohormone which he called Cardiodilatin and portion(s) thereof (U.S. Pat. No. 4,751,284). In this patent Dr. Frossman patented the rat sequence of the ANF prohormone. In his patent he stated that parts of the whole prohormone had activity if the C-terminal end (i.e., ANF) was attached to it. In publications he has stated that the rest of the rat prohormone only has activity if the C-terminus (i.e., ANF with its intact ring structure) of the rat prohormone is attached to it (Frossman W.G., Contr. Nephrol. 50:1–13, 1986) (see Attachment A). Dr. Frossman has never published that other peptide(s) originating from the rat ANF prohormone that he patented have any biologic activity by themselves. Dr. Frossman has further stated on page 11 of Attachment A "I think that the 28 a.a. C-terminal is sufficient for explaining all effects and that an N-terminal fragment does not qualitatively affect the biologic activity ... the synthetic N-terminal segments that we have investigated so far do not exhibit the biologic activity of cardiodilatin". It has been over 10 years since Frossmann submitted his patent and he has never published that any portion of cardiodilatin (i.e., rat ANF prohormone) has any biologic activity if the respective portion is not attached to the ANF portion of cardiodilatin. We have looked at peptides consisting of amino acids 1–30 (i.e., proANF 1–30), amino acids 31–67 (i.e., proANF 31–67) and amino acids 79–98 (i.e., proANF) from the rat ANF prohormone and have found they have no biologic effect(s) (i.e., specifically no blood pressure lowering, sodium excretion or diuretic effects) in the rat or other vertebrate species. Only ANF of the peptides from the rat ANF prohormone had biologic effects.

On the other hand, my Method-of-Use patent is for peptides consisting of amino acids 1–30, 31–67, and 79–98 of the human ANF prohormone (see table 1 for amino acid sequence of human ANF prohormone) which have marked blood pressure lowering, sodium and/or potassium excreting properties in both healthy animals (i.e., rats, Martin et al., Am. J. Physiol. 258:F1401–1408, 1990; Attachment B) and humans (Vesely et al., Circulation 90:1129–1140, 1994; Attachment C). This Method-of-Use application is, thus, for peptides with distinctly different amino acid sequences and also distinctly different biologic properties than rat cardiodilatin and fragments thereof patented by Frossmann. The peptides from the human sequence have potent biologic properties while the peptides consisting of amino acids 1–30, 31–67, and 79–98 of the rat sequence of the ANF have no biologic, physiologic or therapeutic properties by themselves. This Method-of-Use application is not for the rat forms of proANF 1–30, proANF 31–67 or proANF 79–98 but rather the human forms which I discovered have biologic effects in both animals and humans (see Attachments B & C).

Figure 1:
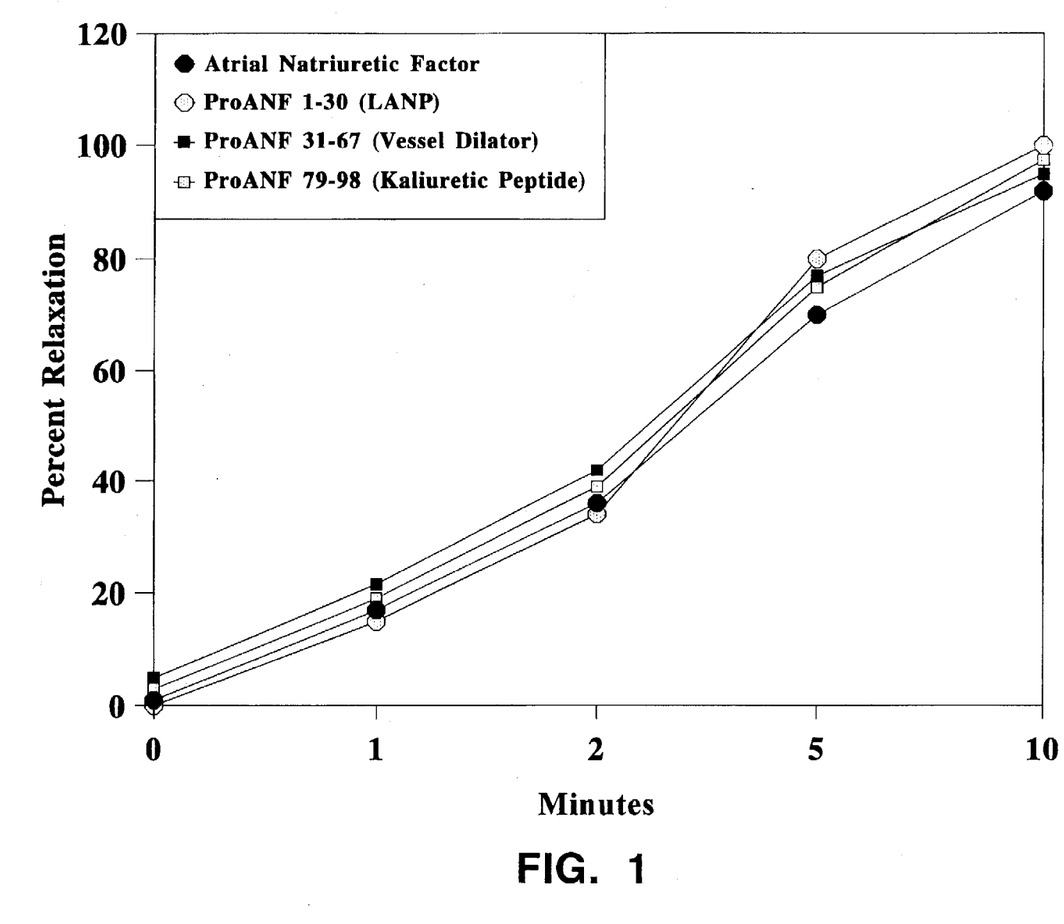
FIG. 1 is a graph comparing the vasodilatory effects of the four peptide hormones originating from human ANF prohormone with respect to relaxation of porcine aorta that had been preconstricted with 0.3 µM phenylephrine.

In addition to the human forms of these peptides having biologic potential in humans as therapy as detailed below, these peptides consisting of amino acids 1–30 (tentatively named long acting natriuretic peptide), amino acids 31–67 (tentatively named vessel dilator) and amino acids 79–98 (tentatively named kaliuretic peptide) are actually peptide hormones since they circulate in humans (FIG. 1, Vesely et al., Circulation 90:1129–1140, 1994; Attachment C; Gower et al., Peptides 15:861–867, 1994) and have biologic effects in other organs (i.e., target tissues) different from the organ or gland from which they are released (Vesely et al., Circulation 90:1129–1140, 1994).

As one observes in FIGS. 2–5, the above enumerated peptide hormones have significant blood pressure lowering, diuretic, sodium and/or potassium excreting properties in healthy humans. It has further been demonstrated that in humans that none of the above delineated peptide hormones work through ANF (i.e., the C-terminus of the ANF prohormone, Vesely et al., J. Clin. Endo. and Metab. 78:1128–1134, 1994; Attachment D).

When one examines the amino acids of the rat prohormone in the Frossmann U.S. Pat. No. 4,751,284, one notes the amino acid sequence of the peptides are distinctly different beginning as early as the 3rd amino acid in the prohormone with his patented sequence being Val-Try-Glyhormone consisting of amino acids 79–98 of the human ANF prohormone has diuretic, kaliuretic (i.e., potassium excreting) and blood pressure lowering properties. (See Table 1 for sequences).

TABLE 1

Amino acid sequence of human ANF prohormone polypeptide (pro-ANF)

1
H—Asn—Pro—Met—Tyr—Asn—Ala—Val—Ser—Asn—Ala—Asp—Leu—Met—

Asp—Phe—Lys—Asn—Leu—Leu—Asp—His—Leu—Glu—Glu—Lys—Met—Pro—

30  31
Leu—Glu—Asp—Glu—Val—Val—Pro—Pro—Gln—Val—Leu—Ser—Glu—Pro—

Asn—Glu—Glu—Ala—Gly—Ala—Ala—Leu—Ser—Pro—Leu—Pro—Glu—Val—

67
Pro—Pro—Trp—Thr—Gly—Glu—Val—Ser—Pro—Ala—Gln—Arg—Asp—Gly—

79
Gly—Ala—Leu—Gly—Arg—Gly—Pro—Trp—Asp—Ser—Ser—Asp—Arg—Ser—

Ala—Leu—Leu—Lys—Ser—Lys—Leu—Arg—Ala—Leu—Leu—Thr—Ala—Pro—

98  99
Arg—Ser—Leu—Arg—Arg—Ser—Ser—Cys—Phe—Gly—Gly—Arg—Met—Asp—Arg—

126
Ile—Gly—Ala—Gln—Ser—Gly—Leu—Gly—Cys—Asn—Ser—Phe—Arg—Tyr—OH

Ser while the same amino acid sequence in the human prohormone is Met-Try-Asn-Ala as in table 1. The presently described human peptides are, thus, distinctly different peptides from those Dr. Frossmann has patented. The changing of a single amino acid in a specific peptide can have profound effects on biologic activity. Thus, the peptides in his patent with markedly different amino acids sequences might be expected to have a difference in biologic properties or no biologic effects (which is the case for the peptides derived from the 98 a.a. N-terminal rat sequence of the ANF prohormone). None of the human peptides in the present Method-of-Use application have a ring structure within their peptide sequence while all of the peptides that Frossmann has stated that have activity in Frossmann's patent are characterized by having a ring structure. This ring structure is thought to be essential for ANF and extended ANF peptides to bind to their receptor while human proANF 1–30 and 31–67 bind to separate and distinct receptors from the ANF receptor(s) (Vesely et al., Peptides 11;193–197, 1990; Vesely et al., J. Clin. Endocrinol. Metab. 71:1138–1146, 1990). The peptides proposed for Method-of-Use in the present patent application are linear peptides. They do not have a ring structure. Further, the human proANF's 1–30, 31–67, and 79–98 in addition to having distinct receptors from ANF also have different mechanisms of action from ANF (Chiou and Vesely: Endocrinology, 136:in press 1995; Attachment E).

SUMMARY OF INVENTION

In vivo animal (Attachment B) and human (Attachment C) testing demonstrate that potent natriuretic, diuretic, and blood pressure reducing effects are exhibited by two peptide hormones originating from the human atrial natriuretic factor (ANF) prohormone consisting of amino acid 1–30 and 31–67 of the human prohormone while another peptide The carboxy terminal 28 amino acid fragment of the pro-ANF prohormone (amino acids 99–126 as shown in Table 1) has been termed alternatively cardioatrin, atrial natriuretic peptide (ANP), and atrial natriuretic factor (ANF).

Figure 2:
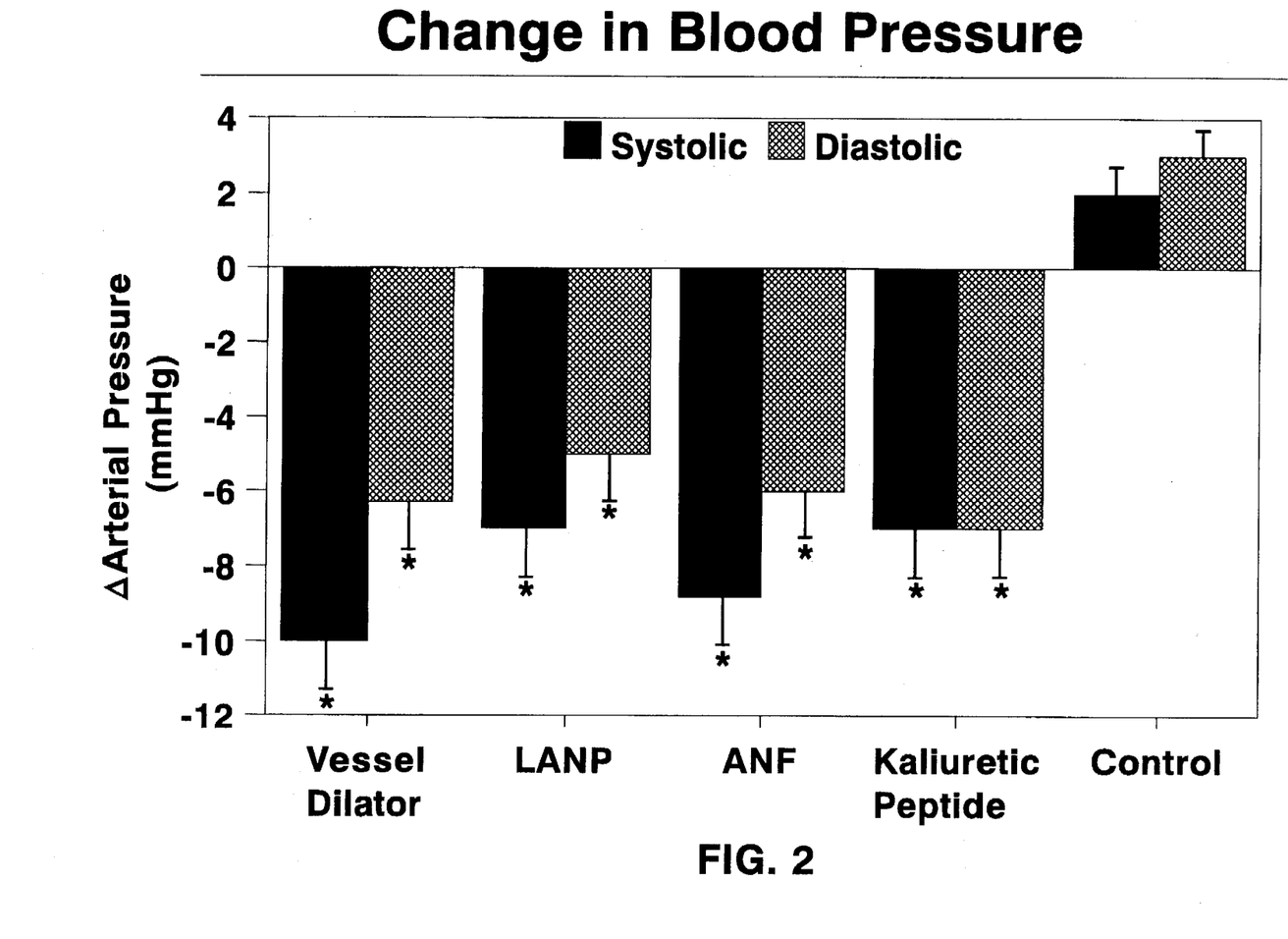
FIG. 2 illustrates the data with respect to human atrial natriuretic factor prohormone peptides (proANFs) 1–30, 31–67, 79–98, and atrial natriuretic factor (ANF) decreasing systolic and diastolic blood pressures in healthy human volunteers. The decreases in both systolic and diastolic blood pressures secondary to proANFs 1–30, 31–67, 79–98, and ANF were significant at the P<0.05 level when evaluated by paired t test. Values are mean±SEM of 6 healthy subjects for each peptide.
Figure 3:
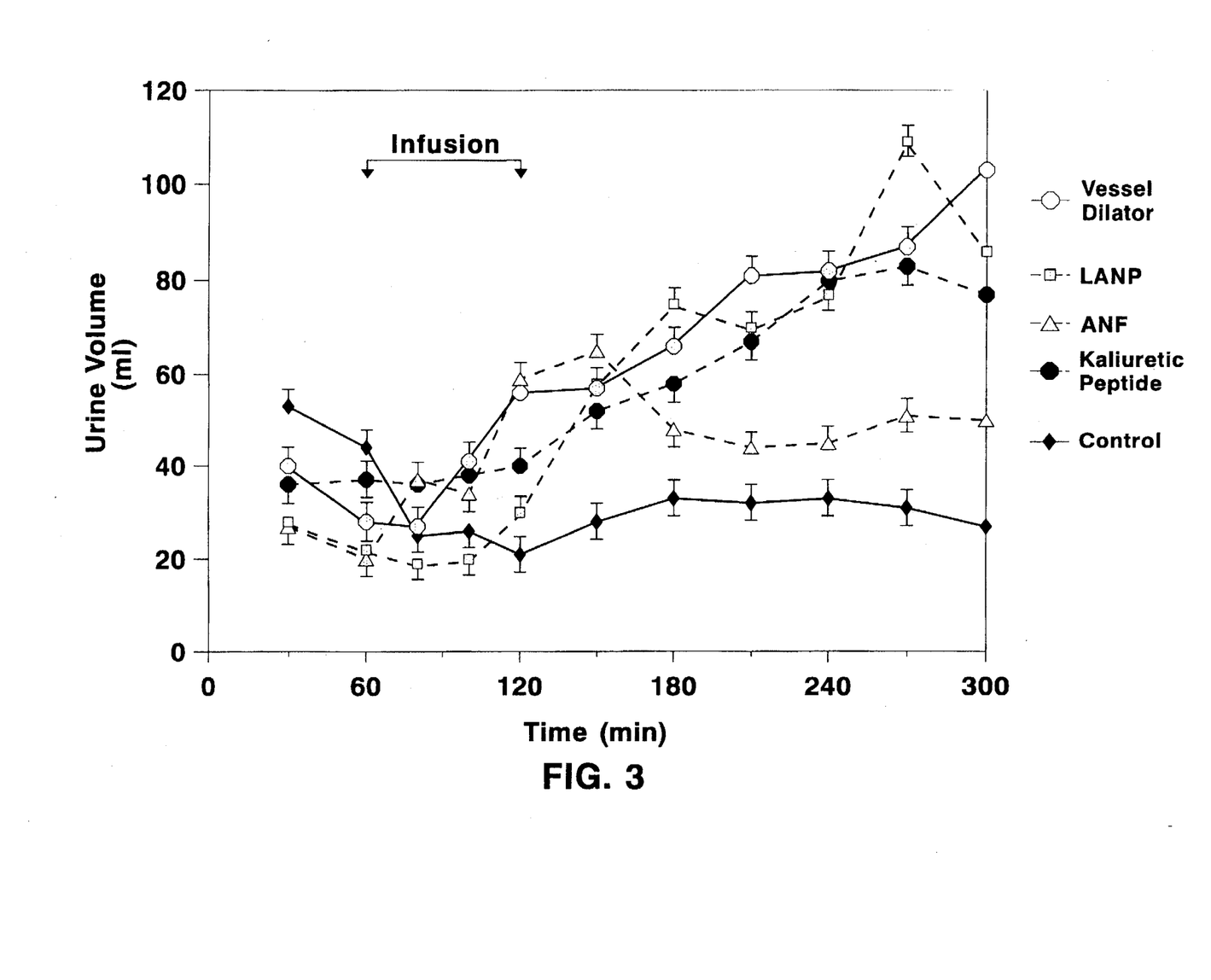
FIG. 3 plot shows influence of human atrial natriuretic factor prohormone peptides 1–30, 31–67, 79–98 and atrial natriuretic factor (ANF) on urine flow in healthy human volunteers. Individual subjects (n=6 for each peptide) received 100 ng/kg body wt per minute of each of the respective peptides for 1 hour by intravenous infusion. The increase in urine volume (in milliliters) secondary to each of the respective peptides was significant at P<0.05 when evaluated by ANOVA. *Time points at which urine flow was significantly (P<0.05) increased compared with baseline urine flow in the same subjects when evaluated by repeated measures of analysis of variance(ANOVA). Mean±SEM values for each peptide at each point are illustrated.
Figure 4:
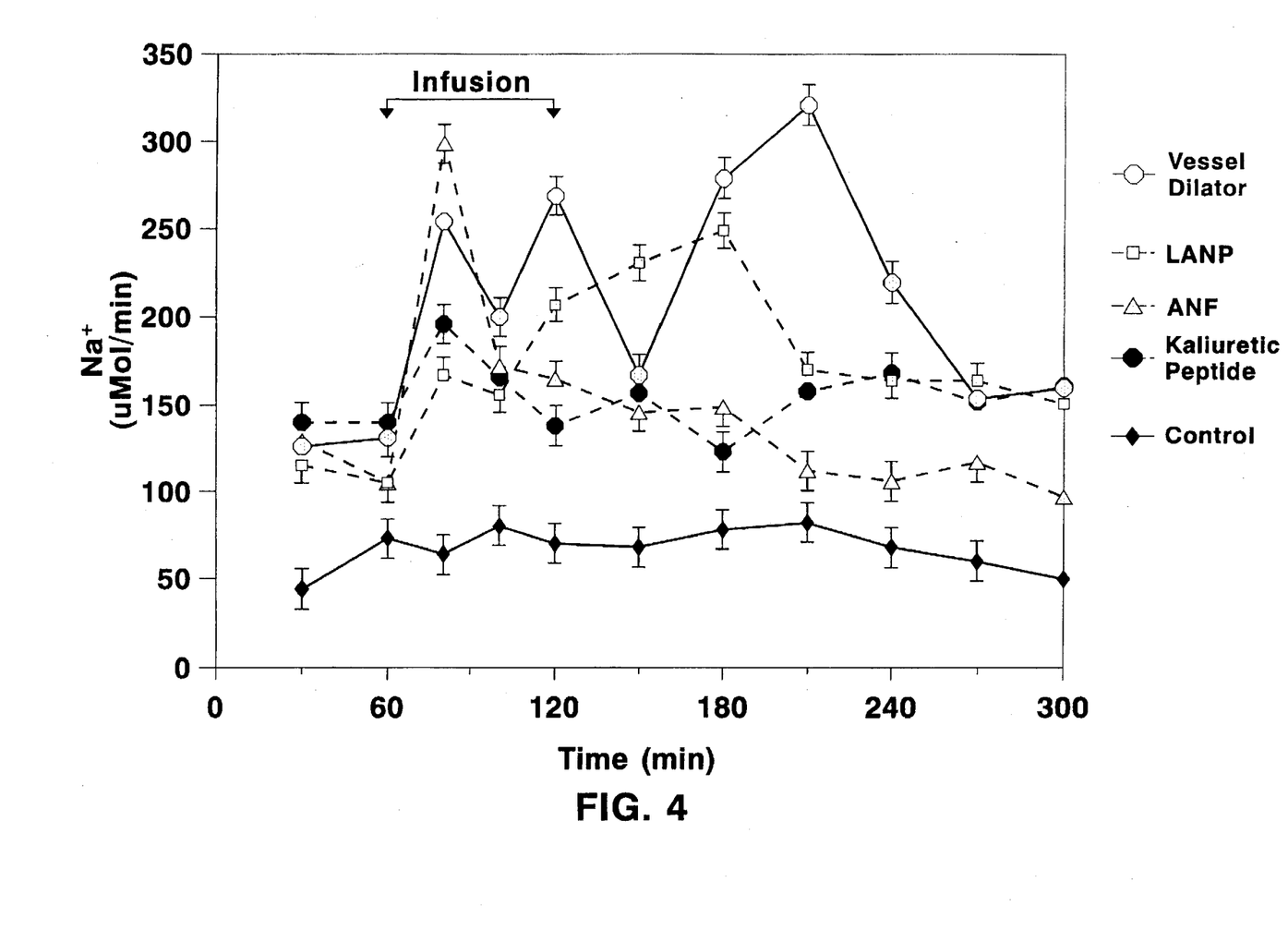
FIG. 4 plot shows effect of human atrial natriuretic factor prohormone peptides (proANFs) 1–30, 31–67, 79–98, and atrial natriuretic factor (ANF) on sodium excretion in healthy human volunteers. When infused at their 100 ng/kg body wt concentration per minute for 60 minutes, each of these respective peptides except proANF 79–98 significantly (P<0.05) increased sodium excretion compared to baseline sodium excretion in the same subjects when evaluated by repeated-measures of ANOVA. Values are mean±SEM values of 6 healthy subjects for each group.

Recent clinical trials in healthy human subjects have demonstrated that these peptides have potent diuretic, blood pressure lowering, natriuretic and/or kaliuretic effects (FIGS. 2–5; Attachment C). In humans as well as in other mammals proANF 1–30 and 31–67 have unique sodium excreting properties compared to ANF with all of ANF's sodium excreting effects ceasing within 30 minutes while proANF 1–30 and 31–67's sodium excreting effects were significantly ($P<0.001$) prolonged compared to ANF (FIG. 4). ProANFs 1–30, 31–67, and 79–98 have significant diuretic properties in humans increasing urine flow 4–12-fold and this increased urine flow was still significantly increased 2–3 hours after stopping their infusions, which also is markedly prolonged compared to ANF (FIG. 3). ProANF 79–98 has the unique property of being the strongest stimulator of potassium excretion of any of the atrial peptides and (FIG. 5) should be useful for treating states associated with hyperkalemia. Each of 3 peptides of the instant invention have significantly prolonged half-lives compared to ANF (Ackermann et al., J. Clin. Pharmacol. 32:415–421, 1992) which in addition to their unique and prolonged effects compared to ANF would cause them to be given less frequently in treatment (and therefore preferred) of conditions characterized by high blood pressure, sodium and water retention or hyperkalemia that were enumerated above.

I have now infused the peptides of this invention into humans with congestive heart failure. ProANFs 1–30, 31–67 and 79–98 cause a marked diuresis in humans with congestive heart failure which is significant ($P<0.01$) for at least 3 hours after stopping their respective infusions (see example VI). The persons with congestive heart failure reported that they felt better after the infusion of these peptides. The instant invention is shown herein to be reduced to therapeutic use in humans with congestive heart failure.

The present invention provides method(s)-of-treatment which use these three 100% pure peptides which are sequenced with an peptide sequencer (and are not derived from natural products such as using heart tissues to isolate these peptides). These peptides are not known to exist in the forms which I am seeking to patent in natural products such as heart or any other animal or plant tissues. In tissues the whole 126 amino acid prohormone is present but the individual distinct peptides proANF 31–67 and proANF 79–98 are not. Pharmaceutical compositions in accordance with the present invention include one or more of the three amino-terminal pro-ANF peptides, or non-toxic salts thereof, dispersed in a pharmaceutically acceptable liquid or solid carrier. The administration of one or more of these peptides, or pharmaceutically acceptable addition of salts thereof, to mammals (especially humans) in accordance with the invention may be carried out for treatment of hypertension, disorders of water and sodium metabolism, (delineated above), hyperkalemia, or to counteract development of congestive heart failure and/or renal failure; in addition, pharmaceutical compositions containing any of the three peptides may be used as a smooth muscle relaxant.

BRIEF DESCRIPTION OF THE DRAWINGS

FIG. 8. Inhibition of renal medullary Na+-K+-ATPase activity by proANF 79–98 (kaliuretic peptide), proANF 1–30 (long acting natriuretic peptide), proANF 31–67 (vessel dilator), and angiotensin II at their $10^{-11}$M concentrations. Atrial natriuretic factor (ANF) ($10^{-11}$M) did not significantly inhibit Na+-K+-ATPase when evaluated by Analysis of Variance (ANOVA), whereas each of the other peptides'inhibition of Na+-K+-ATPase was significant at P<0.01 (*). Naproxen (0.5 mM), a prostaglandin synthesis inhibitor, completely blocked each of these peptides'effects on renal medullary Na+-K+-ATPase with its effect being significantly different (P<0.001) from the effects of each of the peptides (except for ANF, which had no effect by itself) when evaluated by ANOVA followed by Duncan's Multiple Range Text (MRT) (n=6 for each group).

DETAILED DESCRIPTION OF THE INVENTION

The nomenclature used to define the peptides is that specified by Schroder & Luhke, "The Peptides," Academic Press (1965) wherein, in accordance with conventional representation, the amino group appears to the left and the carboxy group to the right. Where the amino acid residue has isomeric forms, it is the L-form of the amino acid that is represented. The invention provides pharmaceutical compositions containing one or more of the peptides originating from the human ANF prohormone consisting of amino acids 1–30, 31–67, 79–98, of this prohormone, i.e., pro-ANF (1–30), pro-ANF (31–67) and pro-ANF (79–98), which have the sequences shown in Table I.

These three peptides may be synthesized by the following suitable techniques: solid-phase techniques, by partial solid-phase techniques, by fragment condensation, by classical solution addition or by an automated 8-channel peptide sequencer which can synthesize up to 8 different 20 residue peptides in 2 days. Examples of the techniques of exclusively solid-state synthesis are set forth in the textbook "Solid-Phase Peptide Synthesis," (Stewart & Young, Freemon & Co., San Francisco, 1969); and examples are the disclosures of U.S. Pat. Nos. 3,842,067 and 3,862,925. Such human peptides are currently being sequenced commercially by automated peptide sequencers from laboratories such as Peninsula Laboratories, Belmont, Calif. Synthesis by the use of recombinant DNA techniques may also be used by suitably employing a structural gene coding for the desired form of the peptide. The synthetic peptides may be obtained by transforming a microorganism, either a procaryote or eucaryote, such as yeast, using an expression vector including a promoter and operator together with such a structural gene and causing such transformed microorganism to express the peptide. A non-human animal may also be used to produce the peptide by gene-farming using such a structural gene or by using microinjection of embryos; the synthetic peptide is then suitably recovered from the animal by extraction from sera or the like.

The following examples demonstrate the therapeutic usefulness of the three human pro-ANF peptides.

EXAMPLE I

Pure synthetic human sequences of the following three human pro-ANF peptides and ANF are tested for vasodilation of porcine aortas (with or without the endothelium present): human pro-ANF 1–30 having the formula H-Asn-Pro-Met-Tyr-Asn-Ala-Val-Ser-Asn-Ala-Asp-Leu-Met-Asp-Phe-Lys-Asn-Leu-Leu-Asp-His-Leu-Glu-Glu-Lys-Met-Pro-Leu-Glu-Asp-OH; pro-ANF 31–67 having the formula H-Glu-Val-Val-Pro-Pro-Gln-Val-Leu-Ser-Glu-Pro-Asn-Glu-Glu-Ala-Gly-Ala-Ala-Leu-Ser-Pro-Leu-Pro-Glu-Val-Pro-Pro-Trp-Thr-Gly-Glu-Val-Ser-Pro-Ala-Gln-Arg-OH; and pro-ANF (79–98) having the formual H-Ser-Ser-Asp-Arg-Ser-Ala-Leu-Leu-Lys-Ser-Lys-Leu-Arg-Ala-Leu-Leu-Thr-Ala-Pro-Arg-OH.

30 Kg pigs are sacrificed, and aortic strips are harvested. The strips are attached to F-60 transducer (Narco-BioSystems, Houston, Tex.) and attached to a physiography (Narco-BioSystems) while being submerged in a muscle tissue bath comprising a Krebs Ringer solution at 37° C., with 95% $O_2$-5% $CO_2$ bubbled through the bath. Percentage vasodilation is measured versus time (as reported in FIG. 1) after preconstriction with 0.3 micromolar phenylephrine. The three pro-ANF peptides show maximal vasodilation ten minutes after the peptides are added to the bath. Furthermore, the vasodilation by all four peptides orginating from the ANF prohormone [(pro-ANF 1–30, pro-ANF 31–67, pro-ANF 79–98, and ANF (also referred to herein as pro-ANF 99–126)] is associated with a four-to-five fold increase in cyclic GMP levels over baseline levels. (Vesely et al., Biochem. Biophys. Res. Comm. 148:1540–1548, 1987).

To determine whether these peptides [(pro-hANF 1–30, pro-hANF 31–67, and pro-hANF 79–98)] do have direct effects on smooth muscle, these three pro-ANF fragments plus ANF are studied with cultured smooth muscle cells. All four peptides [(pro-hANF 1–30, pro-hANF 31–67, pro-hANF 79–98, and pro-hANF 99–126)] of the human sequence of the ANF prohormone increase cyclic GMP levels in the cultured smooth muscle cells, which is caused by activation of particulate guanylate cyclase. Dose response curves reveal that half maximal activation ($ED_{50}$) occurs at a concentration of about 10 nanomolar and maximal activation of quanylate cyclase activity occurs at concentrations of about 1 µM for all four peptides in porcine aorta and in isolated smooth muscle cells. These data demonstrate that pro-hANF 1–30, pro-hANF 31–67 and pro-hANF 79–98 of the human ANF prohormone cause vasodilation and activate the guanylate cyclase-cyclic GMP system. The site of action in the aorta appears to be the smooth muscle cell and not the endothelium for all four of the peptide fragments of prohormone ANF since all 4 peptide's vasodilatory effects are equal with or without endothelium present,

EXAMPLE II

The same three peptides and ANF from Example I are tested using the rat clearance model. Six control rats and six experimental Munich-Wistar rats, each weighing 150–200 grams, are used for each peptide, with catheters being placed in both jugular veins and in the femoral artery. The ureters are cannulated for simultaneous urine collections with femoral artery blood collections.

After inserting the catheters, a stabilization of one hour is allowed. A 10 µg/kg bolus of each of the respective human sequences of the peptides is given via the jugular vein to six experimental rats followed by a sustaining infusion of 0.1 µg/kg/min for 60 minutes. Blood and urine samples are collected at 20 minute intervals during this 60 minute infusion. Table II illustrates the effect of each of these peptides on diuresis and salt excretion. In both the control and experimental animals, hematocrits and plasma sodium values remained at the same levels pre- and post-infusion while blood pressure decreased with each of these peptides (see Attachment B).

TABLE II

Comparison of the effect of peptides from $NH_2$-Terminus of ANF prohormone vs. that of atrial natriuretic factor (COOH-terminus) on sodium excretion and urine flow rate

| Peptides | n | V, µl-min$^{-1}$-g kidney wt$^{-1}$ | $U_{Na}V$, µeq-min$^{-1}$-g kidney wt$^{-1}$ | $FE_{NA}$, % |
|---|---|---|---|---|
| Control | 9 | | | |
| A | | 2.84 ± 0.21 | 52.36 ± 12.05 | 0.026 ± 0.008 |
| B | | 3.37 ± 0.30 | 59.53 ± 21.48 | 0.029 ± 0.011 |
| C | | 3.59 ± 0.40 | 54.30 ± 19.52 | 0.023 ± 0.009 |
| ProANF-(1–30) | 7 | | | |
| A | | 1.83 ± 0.27 | 36.37 ± 8.09 | 0.023 ± 0.002 |
| B | | 3.41 ± 0.48 | 224.30 ± 60.34 | 0.241 ± 0.101 |
| C | | 4.31 ± 0.84 | 384.98 ± 124.39 | 0.285 ± 0.094 |
| ProANF-(31–67) | 6 | | | |
| A | | 2.63 ± 0.24 | 144.08 ± 56.75 | 0.057 ± 0.012 |
| B | | 9.36 ± 3.14 | 1,057.68 ± 371.69 | 0.457 ± 0.156 |
| C | | 8.84 ± 1.86 | 1,077.63 ± 306.10 | 0.444 ± 0.155 |
| ProANF-(79–98) | 6 | | | |
| A | | 2.62 ± 0.70 | 90.88 ± 77.76 | 0.030 ± 0.024 |
| B | | 4.75 ± 1.57 | 363.98 ± 261.85 | 0.200 ± 0.152 |
| C | | 5.16 ± 1.04 | 564.22 ± 315.48 | 0.368 ± 0.273 |
| ANF | 7 | | | |
| A | | 2.89 ± 0.71 | 71.77 ± 23.08 | 0.027 ± 0.011 |
| B | | 11.95 ± 4.28 | 1,526.27 ± 796.50 | 0.415 ± 0.141 |
| C | | 7.26 ± 1.39 | 838.61 ± 222.68 | 0.312 ± 0.090 |

Values are means ± SE; n, no. of experiments; V, urine flow rate; $U_{Na}V$, urinary sodium excretion rate; $FE_{NA}$, fractional excretion of sodium, A, control period; B, 1st 60-min experimental period; C, 2nd 60-min experimental period.

These experiments show that three of the peptides originating from the human ANF prohormone increase both the total excretion of sodium and the fractional urine excretion of sodium. These experiments also establish increased diuresis in mammals for all of these peptides relative to the control, (Table II). Concurrently, during the course of the experiment each of the four peptides significantly (P<0.05) reduced blood pressure. Pro-ANF 79–98, the only peptide which does not significantly increase sodium excretion was shown to be a very significant stimulator of potassium excretion (Attachment B). While ANF has been shown to significantly increase potassium excretion, pro-ANF 31–67 does not cause increased potassium excretion.

EXAMPLE III

Testing is also carried out to determine biologic effects of these peptides by measuring their effects on particulate guanylate activity in the kidney. Human ProANF 1-30, ANF 31-67 and ANF 79-98, as well as hANF, at 1 µM concentrations, all enhance particulate guanylate cyclase from 105,000 g whole kidney homogenates, renal cortical and medullary membranes, and in the isolated distal nephron. The human pro-ANF peptides exhibit nearly equal activity to human ANF in whole kidney homogenates and in renal medullary membranes, while in the isolated distal nephrons, some of the pro-ANF peptides are more active than human ANF itself in enhancing particulate guanylate cyclase activity, with results mirroring the renal clearance of sodium data.

EXAMPLE IV

These peptides i.e., pro ANFs 1-30, 31-67, 79-98 can overcome the negative ionotropic (slowing heartbeat) effect of the calcium channel blocker, Verapamil. This effect suggests that these peptides may be useful for treatment of an overdose of an administered calcium channel blocker.

EXAMPLE V

Infusion of these peptides into healthy human subjects was performed as follows: Human pro-ANF 1-30, pro-ANF 31-67, and pro-ANF 79-98, and hANF (i.e., pro-ANF 31-67, were synthesized by Peninsula Laboratories (Belmont, Calif.). High pressure liquid chromatography (HPLC) analysis was performed on a sample of each of the four peptides to ensure purity. The peptides were dissolved in a sterile 0.9% saline solution to a concentration of 100 µg/ml and dispensed in 2 and 5 ml aliquots into sealed sterile vials. At the time of dispensing, randomly selected vials were tested for pyrogens and sterility. Prior to labeling the vials, the actual peptide content of the dispensed solution were determined by direct radioimmunoassay to account for any possible absorption of the respective peptides to the walls of the vials. All vials were then stored at -80° C. until thawed for individual study.

Normal healthy subjects were chosen on the basis of age (between 20 and 50 years), physical examination and biochemical screenings. The subjects consumed their normal diets prior to testing. The subjects fasted overnight and were tested in the morning in the seated position. Intravenous catheters were placed bilaterally for the administration of pro-hANF 1-30, pro-hANF 31-67, pro-hANF 79-98 and hANF [pro-hANF 99-126] and for blood sampling. After completion of a 45-minute equilibration period, there were three 60-minute phases of the study: baseline, experimental infusion (60 minutes) and recovery (3 hours). The baseline phase consisted of two 30 minute urine collection periods, the experimental phase consisted of three 20 minute urine and plasma collection periods, and the recovery phase consisted of two 30 minute urine and plasma collection periods each hour for three hours post-infusion. Urine output was replaced on a milliliter per milliliter basis throughout the study by administering oral water or orange juice. Urine samples were obtained by voiding at the designated collection periods.

Figure 5:
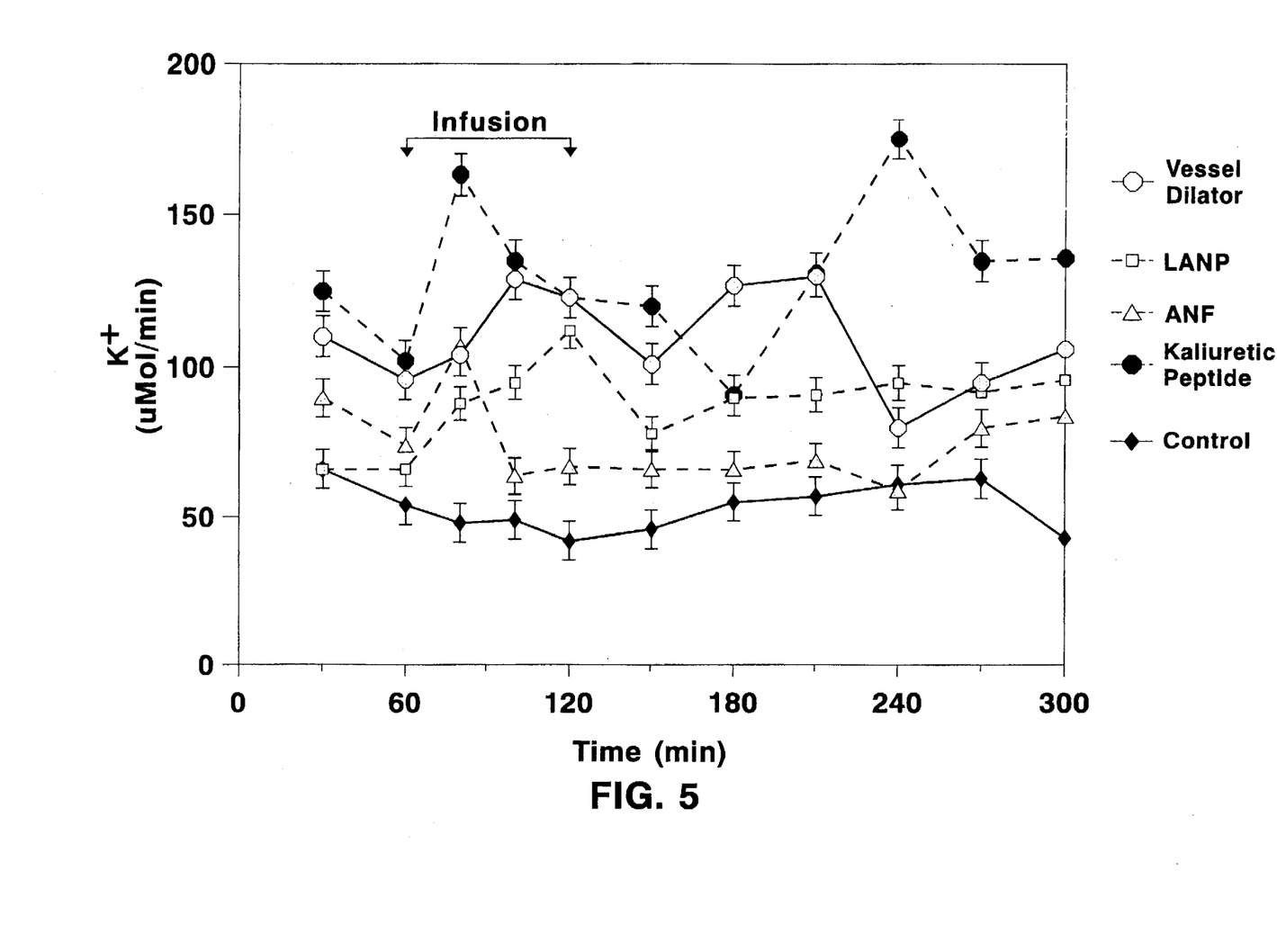
FIG. 5 illustrates the data with respect to human atrial natriuretic factor prohormone peptides (proANFs) 1–30, 31–67, 79–98, and atrial natriuretic factor (ANF) on potassium excretion in healthy humans. Values are mean±SEM of 6 healthy subjects for each peptide. The enhancement of potassium excretion by proANFs 1–30, 79–98, and ANF was significant (P<0.05) when infused at their 100 ng/kg body wt concentrations when evaluated as a group by ANOVA.
Figure 6:
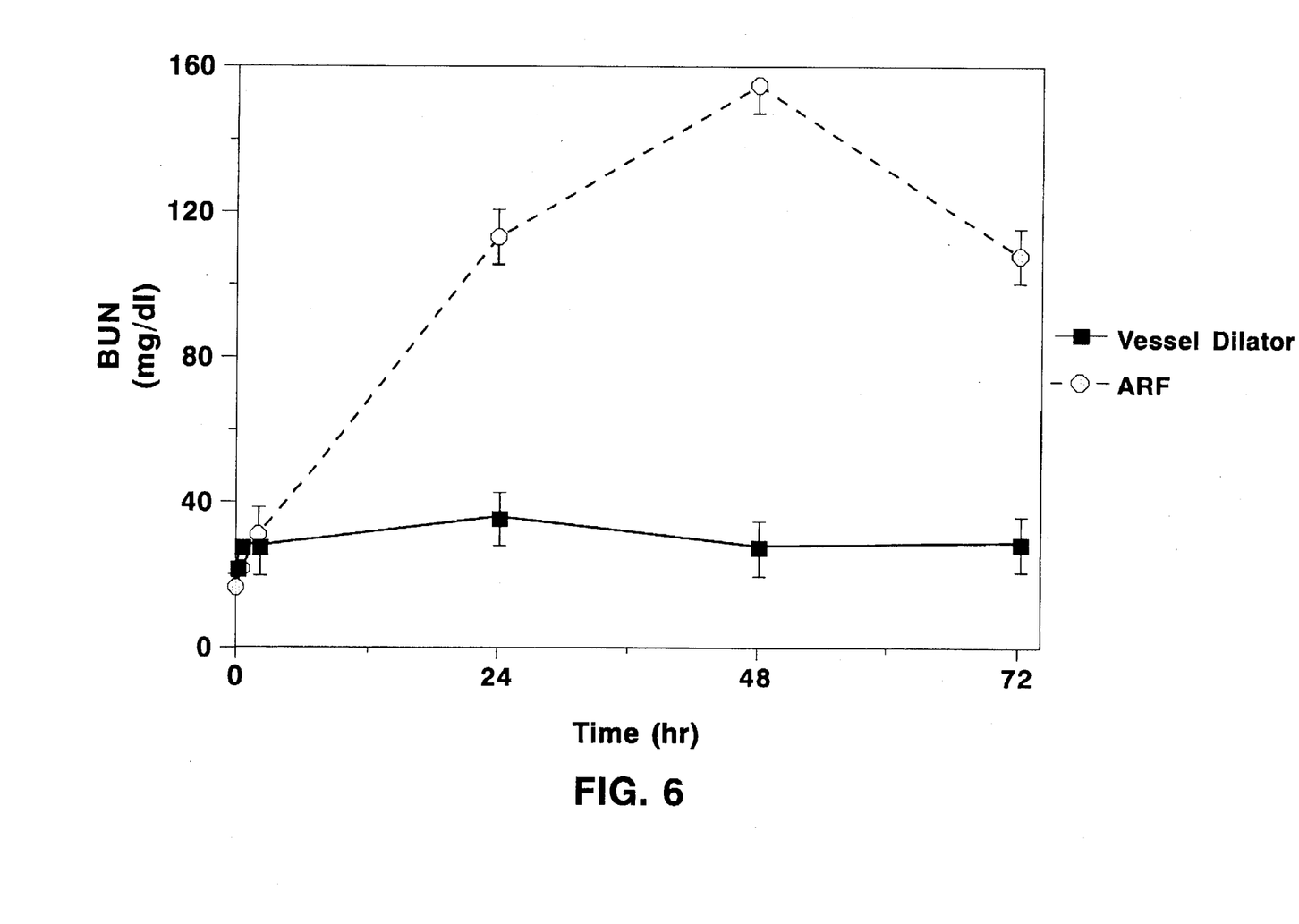
FIG. 6. ProANF 31–67 (i.e., vessel dilator) prevents the rise in blood urea nitrogen (BUN) in rats who have acute renal failure. ARF equals the rats who developed acute renal failure and did not receive proANF 31–67. The BUN increased to over 100 mg/dl in the first 24 hours of acute renal failure and remained above 100 mg/dl after three days while proANF 31–67 completely blocked the increase in BUN in the acute renal failure animals (n=6 for each).
Figure 7:
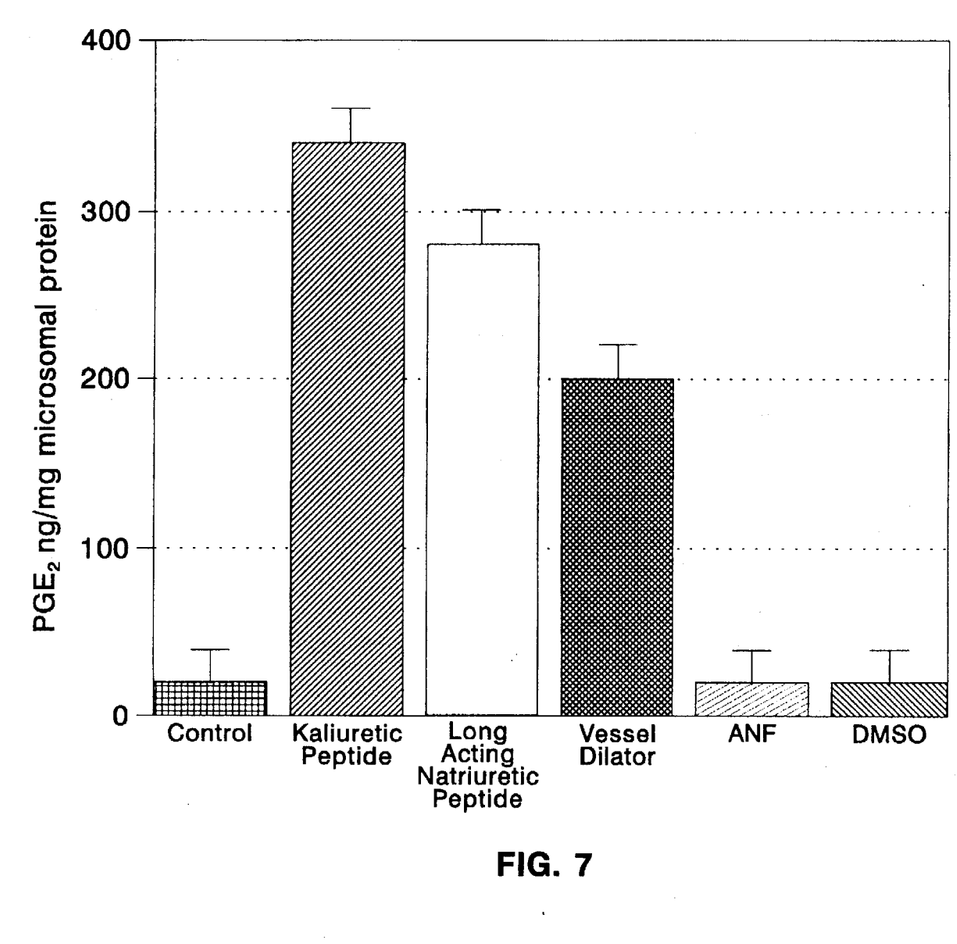
FIG. 7. ProANF 79–98 (kaliuretic peptide), proANF 1–30 (long acting natriuretic peptide), and proANF 31–67 (vessel dilator) each increase prostaglandin $E_2$ ($PGE_2$) synthesis. The increase in $PGE_2$ synthesis by each of these peptides was significant at P<0.05, whereas atrial natriuretic factor (ANF) had no significant effect on $PGE_2$ synthesis when evaluated by Analysis of Variance followed by Duncan's Multiple Range Test (MRT) (n=6).
Figure 8:
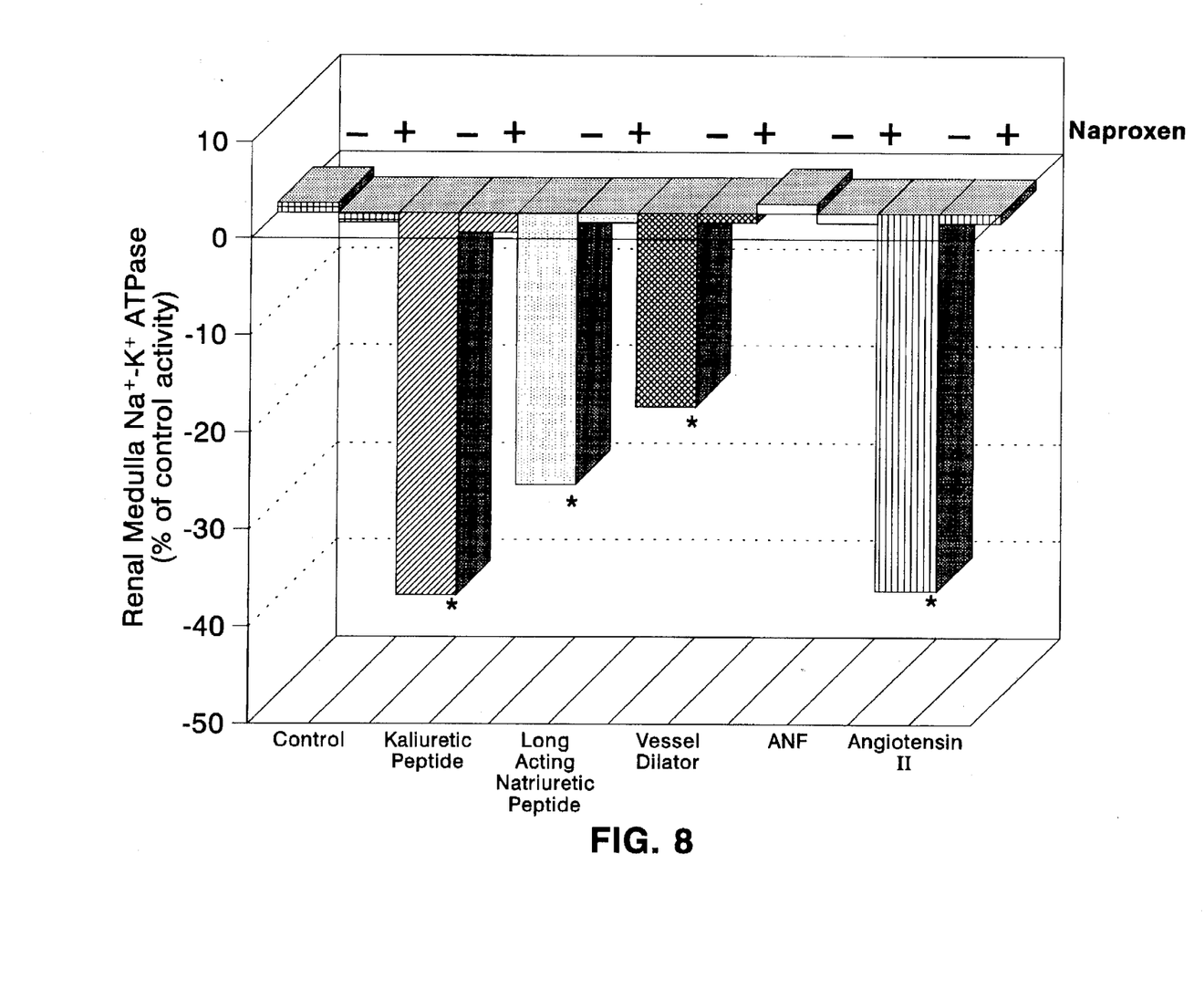

The 36 subjects were divided into 6 groups. One group (i.e., the control group) received a placebo infusion of 0.9% sodium chloride during the experimental infusion phase. While another control group received no infusion whatsoever to determine if the infusion itself has any effect. The four remaining groups of six subjects each received human pro-hANF 1-30, pro-hANF 31-67, pro-hANF 79-98 and hANF. The four groups received the peptides by continuous infusion at the rate of 0.1 µg/kg per minute. The volume administered per hour during the experimental infusion phase was 10 ml for all four peptides and the placebo. All infusions were given by a constant-rate infusion pump, with the final concentrations of prohANFs adjusted for the subjects' body weight. The subjects heart rate and cuff blood pressure were taken at 5 minute intervals throughout the study. The excreted urine was analyzed for sodium concentration. The results of the infusion study are summarized in FIGS. 2-5. The data illustrated in FIG. 2 illustrate that each of these peptides consisting of amino acid 1-30, 31-67, 79-98, and 99-126 of the human sequence of the ANF prohormone have significant blood pressure lowering effects in humans. Each of these peptides also have significant water excreting (i.e., diuretic effects) in humans (FIG. 3). As one observes in FIG. 3, ANF's diuretic effects last less than 60 minutes, while the diuretic effects of proANF 1-30, proANF 31-67, and proANF 79-98 are still significant in humans 3 hours after stopping their respective infusions. This ability to cause a diuresis significantly (P<0.001) longer than ANF is a property that causes these peptides to be preferred over ANF in the treatment of water retaining states, as demonstrated in example VI of humans with congestive heart failure. ProANF 1-30 and proANF 31-67 have significant natriuretic (i.e., sodium excreting) properties in humans that last significantly (P<0.001) longer than ANF's effects (FIG. 4). ProANF 79-98 was found to have the property of being a significant (P<0.01) enhancer of potassium excretion in humans (FIG. 5).

EXAMPLE VI

Human proANF's 1-30, 31-67, 79-98, and 99-126 (i.e., ANF) were infused into human subjects with class II New York Heart Association congestive heart failure. An identical protocol to that used in example V where these peptides were infused into healthy human subjects was utilized. (See Attachment C for a detailed description of this protocol). The human subjects with congestive heart failure received an identical dose (0.1 µg/kg body wt/minute for 60 minutes) that the healthy human subjects received. With infusion of proANF 31-67, urine output doubled in 20 minutes and increased to 7-fold at the end of the 60 minute infusion. The urine output continued to increase after stopping the infusion of pro ANF 31-67 and at 3 hours after stopping the infusion the urine output of the individuals with congestive heart failure was 10-fold that of pre-infusion values (i.e., 320 mls vs 30 mls of urine output per 30 minute period). This striking urine output secondary to proANF 31-67 was significant at P<0.0001 compared to the pre-infusion output of the congestive heart failure subjects (n=6). Pro ANF's 1-30 and 79-98, likewise, caused a significant diuresis in the congestive heart failure individuals (n=6 for each group) with urine output increasing 3- to 6-fold at the end of their respective infusions and the urine flow secondary to these peptides still be elevated (P<0.01) 3 hours after stopping their infusions. ANF's effects, on the other hand, were blunted in the human subjects with congestive heart failure. ANF increased urine flow 2-fold in the congestive heart failure subjects compared to its ability to increase urine flow 4- to 11-fold in healthy human subjects. Thus, proANF 1-30, 31-67, and 79-98 each have stronger diuretic properties than ANF in congestive heart failure patients. These peptides' effects on producing a diuresis whereby they were still markedly enhancing urine flow 3 hours after their infusions had ceased indicate that they definitely have utility in treating humans with congestive heart failure.

Sodium excretion also increased in the human subjects with congestive heart failure three-to-eight fold with proANF 1–30 and 31–67 while ANF's effects on sodium excretion was blunted (i.e., only 1-fold) in persons with congestive heart failure compared to a 3- to 11-fold increase in healthy humans. ProANF 79–98 had no significant increase in sodium excretion in the human subjects with congestive heart failure. This series of investigations demonstrates that proANF 1–30 and proANF 31–67 have utility as treatment of congestive heart failure in humans with strong diuretic and sodium excreting properties in persons with congestive heart failure. The data of these investigations further suggest utility of proANF 79–98 as treatment of congestive heart failure based upon its diuretic (i.e., water excreting properties). One can foresee that when water and sodium balance have been improved by proANF 1–30 and/or proANF 31–67, one might want to maintain this balance by utilizing an agent (i.e., proANF 79–98) that increases water excretion only. One skilled in the art of medicine can, thus, foresee that proANF 1–30 and/or proANF 31–67 may have proANF 79–98 added sequentially as part of a treatment regimen of persons with congestive heart failure (and other sodium and water retaining states) to help maintain their sodium and water balance.

This investigation in human subjects with congestive heart failure (which has not been published in any form) demonstrates the utility of the human forms proANF 1–30, proANF 31–67 and proANF 79–98 in the most common disease (i.e., congestive heart failure) characterized by sodium and water retention. One would anticipate that these peptides would also be useful in other less common forms of salt and water retention (delineated above) since their therapeutic effects would be the same in all diseases characterized by sodium and water retention, i.e., their therapeutic benefit derives from their ability to increase sodium and water excretion in humans and other mammals.

The data in Example V (which includes FIGS. 2–5) demonstrate that the human forms proANF 1–30, 31–67, and 79–98 have similar effects in humans as they do in other mammals. In healthy humans proANF 31–67 lowers blood pressure the most and one would, thus, discern that it may be the most useful therapeutically for lowering blood pressure in humans. It is important to note that each of the above peptides lower blood pressure in humans and therefore using one or more of these peptides in combination may have added therapeutic benefit.

Example VI demonstrates that proANFs 1–30, 31–67 and 79–98 have therapeutic benefit in humans with congestive heart failure. Since these peptides work similarly in all diseases characterized by sodium and water retention by increasing sodium and water excretion, one would expect that each of these peptides will work in all human (and mammals) diseases characterized by sodium and water retention. It may be desirable to administer combinations of two of the three peptides or to administer all three peptides, either simultaneously or in separate preparations, to take advantage of the different biologic effects and potencies of the three peptides in an effective, synergistic therapeutic treatment.

Thus, any one of the three peptide fragments or a non-toxic salt thereof, combined with a pharmaceutically acceptable carrier to form a pharmaceutical composition, may be administered to mammals, including humans, either intravenously, subcutaneously, transdermally, intramuscularly or percutaneously, or through mucosal membranes intranasally. The peptide(s) should be at least about 95% pure and preferably should have a purity of 100%. This purity means that the intended peptide constitutes the stated weight (%) of all like peptides and peptide present. Administration should be prescribed by a physician for humans and by a veterinarian for all other mammals, and the dosage will vary with the particular condition being treated.

Peptides similar to proANF 1–30, proANF 31–67, and proANF 79–98 are often administered in the form of pharmaceutically acceptable non-toxic salts, such as acid addition salts or metal complexes, e.g., with zinc, iron, calcium, barium, magnesium, aluminum or the like (which are considered as addition salts for purposes of this application). Illustrative of such acid addition salts are hydrochloride, hydrobromide, sulphate, phosphate, tannate, oxalate, fumarate, gluconate, alginate, maleate, acetate, citrate, benzoate, succinate, malate, ascorbate, tartrate and the like.

The peptides should be administered to humans under the guidance of a physician, and pharmaceutical compositions will usually contain the peptide in conjunction with a conventional, pharmaceutically-acceptable carrier. The dosage may be from about 0.1 to about 200 micrograms of the peptide per kilogram of the body weight of the host depending on the specific condition being treated.

Particular features of the invention are emphasized in the claims which follow.

What is claimed is:

1. A method of treating high blood pressure, congestive heart failure, pulmonary edema, toxemia of pregnancy, nephrotic syndrome, acute and chronic renal failure, hepatic cirrhosis with and without ascites; which method comprises administering to a mammal, including humans, a therapeutically effective amount of at least 95% pure synthetic peptide from the group of peptides consisting of amino acids 1-30 (i.e., proANF 1-30), amino acids 31-67 (i.e., proANF 31-67), and amino acids 79-98 (i.e., proANF 79-98) of the human sequence of the 126 amino acid atrial natriuretic factor prohormone; which have blood pressure lowering, water, sodium and/or potassium excreting properties in humans; and combinations thereof or a non-toxic salt thereof.

2. A method according to claim 1 wherein said peptide (proANF 1-30) has the following sequence: H-Asn-Pro-Met-Tyr-Asn-Ala-Val-Ser-Asn-Ala-Asp-Leu-Met-Asp-Phe-Lys-Asn-Leu-Leu-Asp-His-Leu-Glu-Glu-Lys-Met-Pro-Leu-Glu-Asp-OH, synthesized with an automated peptide synthesizer or other in vitro peptide synthesis techniques.

3. A method according to claim 1 wherein said peptide (proANF 31-67) has the sequence: H-Glu-Val-Val-Pro-Pro-Gln-Val-Leu-Ser-Glu-Pro-Asn-Glu-Glu-Ala-Gly-Ala-Ala-Leu-Ser-Pro-Leu-Pro-Glu-Val-Pro-Pro-Trp-Thr-Gly-Glu-Val-Ser-Pro-Ala-Gln-Arg-OH, synthesized with an automated peptide syntesizer or other in vitro peptide synthesis techniques.

4. A method according to claim 1 wherein said peptide (proANF 79-98) has the sequence: H-Ser-Ser-Asp-Arg-Ser-Ala-Leu-Leu-Lys-Ser-Lys-Leu-Arg-Ala-Leu-Leu-Thr-Ala-Pro-Arg-OH, synthesized with an automated peptide synthesizer or other in vitro synthesis techniques.

5. A method according to claim 1 wherein said peptide(s) being of at least 95% pure or a non-toxic salt thereof is administered in a pharmaceutically acceptable liquid or solid carrier.

6. A method in accordance with claim 1 wherein said administration is carried out intravenously, subcutaneously, transdermally, percutaneously, intramuscularly, or via mucous membranes such as in a nasal spray.

7. A method in accordance with claim 2 wherein said administration is carried out intravenously, subcutaneously, transdermally, percutaneously, intramuscularly, or via mucous membranes such as in a nasal spray.

8. A method in accordance with claim 3 wherein said administration is carried out intravenously, subcutaneously, transdermally, percutaneously or intramuscularly, or via mucous membranes such as in a nasal spray.

9. A method in accordance with claim 4 wherein said administration is carried out intravenously, subcutaneously, transdermally, percutaneously, intramuscularly, or via mucous membranes such as in a nasal spray.

10. A method of claim 1 wherein said administration is at a level between about 0.1 and 200 micrograms per kilogram of body weight.

11. A method of claim 2 wherein said administration is at a level between about 0.1 and 200 micrograms per kilogram of body weight.

12. A method of claim 3 wherein said administration is at a level between about 0.1 and 200 micrograms per kilogram of body weight.

13. A method of claim 4 wherein said administration is at a level between about 0.1 and 200 micrograms per kilogram of body weight.

14. An alternate method in accordance with claim 1 wherein a combination of at least two of said peptides is administered.

15. An alternate method in accordance with claim 1 wherein proANF 1-30 is administered in combination with proANF 31-67.

16. An alternate method in accordance with claim 1 wherein proANF 1-30 is administered in combination with proANF 79-98.

17. An alternate method in accordance with claim 1 wherein proANF 31-67 is administered in combination with proANF 79-98.

18. An alternate method in accordance with claim 1 wherein proANF 1-30, proANF 31-67, and proANF 79-98 are administered together.

19. A pharmaceutical composition for treating high blood pressure, congestive heart failure, nephrotic syndrome, acute and chronic renal failure, toxemia of pregnancy, pulmonary edema, and hepatic cirrhosis, which composition consists essentially of a therapeutically effective amount of at least 98% pure synthetic human peptide which is selected from the group of proANF 1-30, proANF 31-67, proANF 79-98 and a combination thereof or non toxic salts thereof, plus a pharmaceutically acceptable liquid or solid carrier.

20. A composition according to claim 19 wherein said peptide (proANF 1-30) has the following sequence: H-Asn-Pro-Met-Tyr-Asn-Ala-Val-Ser-Asn-Ala-Asp-Leu-Met-Asp-Phe-Lys-Asn-Leu-Leu-Asp-His-Leu-Glu-Glu-Lys-Met-Pro-Leu-Glu-Asp-OH.

21. A composition according to claim 19 wherein said peptide (proANF 31-67) has the sequence: H-Glu-Val-Val-Pro-Pro-Gln-Val-Leu-Ser-Glu-Pro-Asn-Glu-Glu-Ala-Gly-Ala-Ala-Leu-Ser-Pro-Leu-Pro-Glu-Val-Pro-Pro-Trp-Thr-Gly-Glu-Val-Ser-Pro-Ala-Gln-Arg-OH.

22. A composition according to claim 19 wherein said peptide (proANF 79-98) has the sequence: H-Ser-Ser-Asp-Arg-Ser-Ala-Leu-Leu-Lys-Ser-Lys-Leu-Arg-Ala-Leu-Leu-Thr-Ala-Pro-Arg-OH.

23. A method of treating sodium and water retaining conditions which include congestive heart failure, renal failure, toxemia of pregnancy, and hepatic cirrhosis with ascites comprising administering to a human a therapeutically effective amount of a 100% pure synthetic peptide from the group consisting of the human sequences proANF 1-30, proANF 31-67, proANF 79-98 and combinations thereof or a non-toxic salt thereof.

24. A method of regulating hypertension comprising administering to a human a therapeutically effective amount of at least 95% pure, synthetic peptide form the group of peptides consisting of the human sequenced proANF 1-30, proANF 31-67, proANF 79-98 and a combination thereof or a non-toxic salt thereof.

25. A method of treating hyperkalemia (i.e., high blood potassium) associated with acidosis, digitalis overdosage, succinylcholine, insulin deficiency, acute and chronic renal failure, Addison's disease (i.e., adrenal insufficiency) and the hypoaldosteronism comprised of administering to humans and other mammals a therapeutically effective amount of proANF 79-98 or proANF 1-30 or a combination thereof or non-toxic salt thereof.

* * * * *

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
  ( A ) LENGTH: 30 amino acids
  ( B ) TYPE: Amino acid
  ( C ) STRANDEDNESS:
  ( D ) TOPOLOGY: linear  ( i i ) MOLECULE TYPE:
  ( A ) DESCRIPTION: Peptide consisting of 30 amino acids
   constituting N- terminal 30 amino acids of 126 amino acid
   atrial natriuretic (iii) HYPOTHETICAL: No (iv) ANTI-SENSE: No (v) FRAGMENT TYPE: N-terminal fragment (vi) ORIGINAL SOURCE: Genomic mRNA
   (A) ORGANISM: Homo Sapiens
   (B) STRAIN:
   (C) INDIVIDUAL ISOLATE:
   (D) DEVELOPMENTAL STAGE:
   (E) HAPLOTYPE:
   (F) TISSUE TYPE: Heart muscle
   (G) CELL TYPE: myocyte
   (H) CELL LINE:
   (I) ORGANELLE:

(viii) IMMEDIATE SOURCE:
   (A) LIBRARY:
   (B) CLONE:

(viii) POSITION IN GENOME:
   (A) CHROMOSOME/SEGMENT: Distal short arm of Chromosome 1 in band 1 P36
   (B) MAP POSITION: band 1
   (C) UNITS: P36

(ix) FEATURE:
   (A) NAME/KEY: ProANF 1-30
   (B) LOCATION: First 30 amino acids from N-terminus of atrial natriuretic factor prohormone.
   (C) IDENTIFICATION METHOD: Infusion of peptide into animals and humans.
   (D) OTHER INFORMATION: Lowers blood pressure, causes a diuresis and enhances sodium excrement in humans.

(x) PUBLICATION INFORMATION:
   (A) AUTHORS: Vesely, David L, Douglass, Margaret A, Dietz, John R, Gower, William R Jr, McCormick, Michael T, Rodrigues-Paz, George, Schocken, Douglas D
   (B) TITLE: Three peptides from atrial natriuretic factor prohormone amino terminus lower blood pressure and produce diuresis, natriuresis, and/or kaliuresis in humans.
   (C) JOURNAL: Circulation
   (D) VOLUME: 90
   (E) ISSUE: 3
   (F) PAGES: 1129-1140
   (G) DATE: September, 1994
   (H) DOCUMENT NUMBER:
   (I) FILING DATE:
   (J) PUBLICATION DATE:
   (K) RELEVANT RESIDUES IN SEQ ID NO: 30

(xi) SEQUENCE DESCRIPTION: SEQ ID NO:1:

Asn Pro Met Tyr Asn Ala Val Ser Asn Ala Asp Leu Met Asp Phe Lys
1               5                   10                  15
Asn Leu Leu Asp His Leu Glu Glu Lys Met Pro Leu Glu Asp
            20                  25                  30

(2) INFORMATION FOR SEQ ID NO:2:

(i) SEQUENCE CHARACTERISTICS:
   (A) LENGTH: 37 amino acids
   (B) TYPE: Amino acid
   (C) STRANDEDNESS:
   (D) TOPOLOGY: linear (ii) MOLECULE TYPE:
   (A) DESCRIPTION: Peptide consisting of 37 amino acids originating in middle of 126 amino acid atrial natriuretic factor prohormone (i.e., amino acids 31-67 of this 126 amino acid prohormone).

(iii) HYPOTHETICAL: No (iv) ANTI-SENSE: No (v) FRAGMENT TYPE: middle fragment of ANF prohormone (vi) ORIGINAL SOURCE: Genomic mRNA
  (A) ORGANISM: Homo Sapiens
  (B) STRAIN:
  (C) INDIVIDUAL ISOLATE:
  (D) DEVELOPMENTAL STAGE:
  (E) HAPLOTYPE:
  (F) TISSUE TYPE: Heart muscle
  (G) CELL TYPE: myocyte
  (H) CELL LINE:
  (I) ORGANELLE:

(vii) IMMEDIATE SOURCE:
  (A) LIBRARY:
  (B) CLONE:

(viii) POSITION IN GENOME:
  (A) CHROMOSOME/SEGMENT: Distal short arm of Chromosome 1 band 1 P36
  (B) MAP POSITION: band 1
  (C) UNITS: P36

(ix) FEATURE:
  (A) NAME/KEY: ProANF 31-67
  (B) LOCATION: 37 amino acids from middle of atrial natriuretic factor prohormone consisting of amino acids 31-67 of this prohormone.
  (C) IDENTIFICATION METHOD: Infusion of peptide into animals and humans.
  (D) OTHER INFORMATION: Lowers blood pressure, causes a diuresis and enhances sodium excrement in humans.

(x) PUBLICATION INFORMATION:
  (A) AUTHORS: Vesely, David L, Douglass, Margaret A, Dietz, John R, Gower, William R Jr, McCormick, Michael T, Rodrigues-Paz, George, Schocken, Douglas D
  (B) TITLE: Three peptides from atrial natriuretic factor prohormone amino terminus lower blood pressure and produce diuresis, natriuresis, and/or kaliuresis in humans.
  (C) JOURNAL: Circulation
  (D) VOLUME: 90
  (E) ISSUE: 3
  (F) PAGES: 1129-1140
  (G) DATE: September, 1994
  (H) DOCUMENT NUMBER:
  (I) FILING DATE:
  (J) PUBLICATION DATE:
  (K) RELEVANT RESIDUES IN SEQ ID NO: 37

(xi) SEQUENCE DESCRIPTION: SEQ ID NO:2:

Glu Val Val Pro Pro Gln Val Leu Ser Glu Pro Asn Glu Glu Ala Gly
1               5                   10                  15

Ala Ala Leu Ser Pro Leu Pro Glu Val Pro Pro Trp Thr Gly Glu Val
        20                  25                  30

Ser Pro Ala Gln Arg
        35

(2) INFORMATION FOR SEQ ID NO:3:

(i) SEQUENCE CHARACTERISTICS:
    (A) LENGTH: 20 amino acids
    (B) TYPE: Amino acid
    (C) STRANDEDNESS:
    (D) TOPOLOGY: linear (ii) MOLECULE TYPE:
    (A) DESCRIPTION: Peptide consisting of 20 amino acids (i.e., amino acids 79-98) from middle of 126 amino acid atrial natriuretic factor prohormone.

(iii) HYPOTHETICAL: No (iv) ANTI-SENSE: No

```
        (v) FRAGMENT TYPE: middle fragment (vi) ORIGINAL SOURCE: Genomic mRNA
                (A) ORGANISM: Homo Sapiens
                (B) STRAIN:
                (C) INDIVIDUAL ISOLATE:
                (D) DEVELOPMENTAL STAGE:
                (E) HAPLOTYPE:
                (F) TISSUE TYPE: Heart muscle
                (G) CELL TYPE: myocyte
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT: Distal short arm of Chromosome 1 band
                    1 P36
                (B) MAP POSITION: band 1
                (C) UNITS: P36

(ix) FEATURE:
                (A) NAME/KEY: ProANF 79-98
                (B) LOCATION: 20 amino acids from middle of atrial
                    natriuretic factor prohormone consisting of amino acids
                    79-98 of 126 amino acid prohormone.
                (C) IDENTIFICATION METHOD: Infusion of peptide into animals
                    and humans.
                (D) OTHER INFORMATION: Lowers blood pressure, causes a
                    diuresis and enhances potassium excretion in humans.

(x) PUBLICATION INFORMATION:
                (A) AUTHORS: Vesely, David L, Douglass, Margaret A, Dietz,
                    John R, Gower, William R Jr, McCormick, Michael T,
                    Rodrigues-Paz, George, Schocken, Douglas D
                (B) TITLE: Three peptides from atrial natriuretic factor
                    prohormone amino terminus lower blood pressure and
                    produce diuresis, natriuresis, and/or kaliuresis in
                    humans.
                (C) JOURNAL: Circulation
                (D) VOLUME: 90
                (E) ISSUE: 3
                (F) PAGES: 1129-1140
                (G) DATE: September, 1994
                (H) DOCUMENT NUMBER:
                (I) FILING DATE:
                (J) PUBLICATION DATE:
                (K) RELEVANT RESIDUES IN SEQ ID NO: 20

(xi) SEQUENCE DESCRIPTION: SEQ ID NO:3:

Ser  Ser  Asp  Arg  Ser  Ala  Leu  Leu  Lys  Ser  Lys  Leu  Arg  Ala  Leu  Leu
 1              5                        10                       15
Thr  Ala  Pro  Arg
             20
```